United States Patent [19]
Messner et al.

[11] Patent Number: 5,987,960
[45] Date of Patent: Nov. 23, 1999

[54] TOOL CALIBRATOR

[75] Inventors: Dale A. Messner, Uniontown; Patrick A. Dayton, Munroe Falls, both of Ohio

[73] Assignee: Picker International, Inc., Cleveland, Ohio

[21] Appl. No.: 08/938,210

[22] Filed: Sep. 26, 1997

[51] Int. Cl.⁶ .................................................. G01C 17/38
[52] U.S. Cl. .............................................................. 73/1.79
[58] Field of Search ................................... 73/1.79, 1.81, 73/104; 348/135, 142, 61; 606/130

[56] References Cited

U.S. PATENT DOCUMENTS

| | | | |
|---|---|---|---|
| 5,181,416 | 1/1993 | Evans .......................................... | 73/104 |
| 5,186,174 | 2/1993 | Schlöndorff et al. . | |
| 5,383,454 | 1/1995 | Bucholz . | |
| 5,494,034 | 2/1996 | Schlondorff et al. . | |
| 5,517,990 | 5/1996 | Kalfas et al. . | |
| 5,552,822 | 9/1996 | Nallakrishnan ........................... | 73/104 |

OTHER PUBLICATIONS

"A Frameless Stereotaxic Operating Microscope for Neurosurgery", Eric M. Friets, et al.; IEEE Transactions on Biomedical Engineering, vol. 36, No. 6, Jun. 1989 pp. 608–617.

"A frameless stereotaxic integration of computerized tomographic imaging and the operating microscope", David W. Roberts, M.D., et al.; J. Neurosurg; vol. 65; Oct. 1986; pp. 545–549.

*Primary Examiner*—Robert Raevis
*Attorney, Agent, or Firm*—Timothy B. Gurin; John J. Fry; Eugene E. Clair

[57] ABSTRACT

A tool calibrator includes two portions shaped to slidably engage and secure a tool in a desired position. The tool is secured by a series of staggered V shaped grooves on each of the two portions having a known geometrical relationship with a diameter of a tool head of the tool. The tool calibrator further includes at least one position signaling device for communicating a location of the tool calibrator in an operating room or other area. A position and direction of a tip of the tool is determined by comparing a location of the tool secured within the tool calibrator to the location of each of the two portions. Further, based on the location of each of the two portions, the diameter of the tool head is calculated.

25 Claims, 8 Drawing Sheets

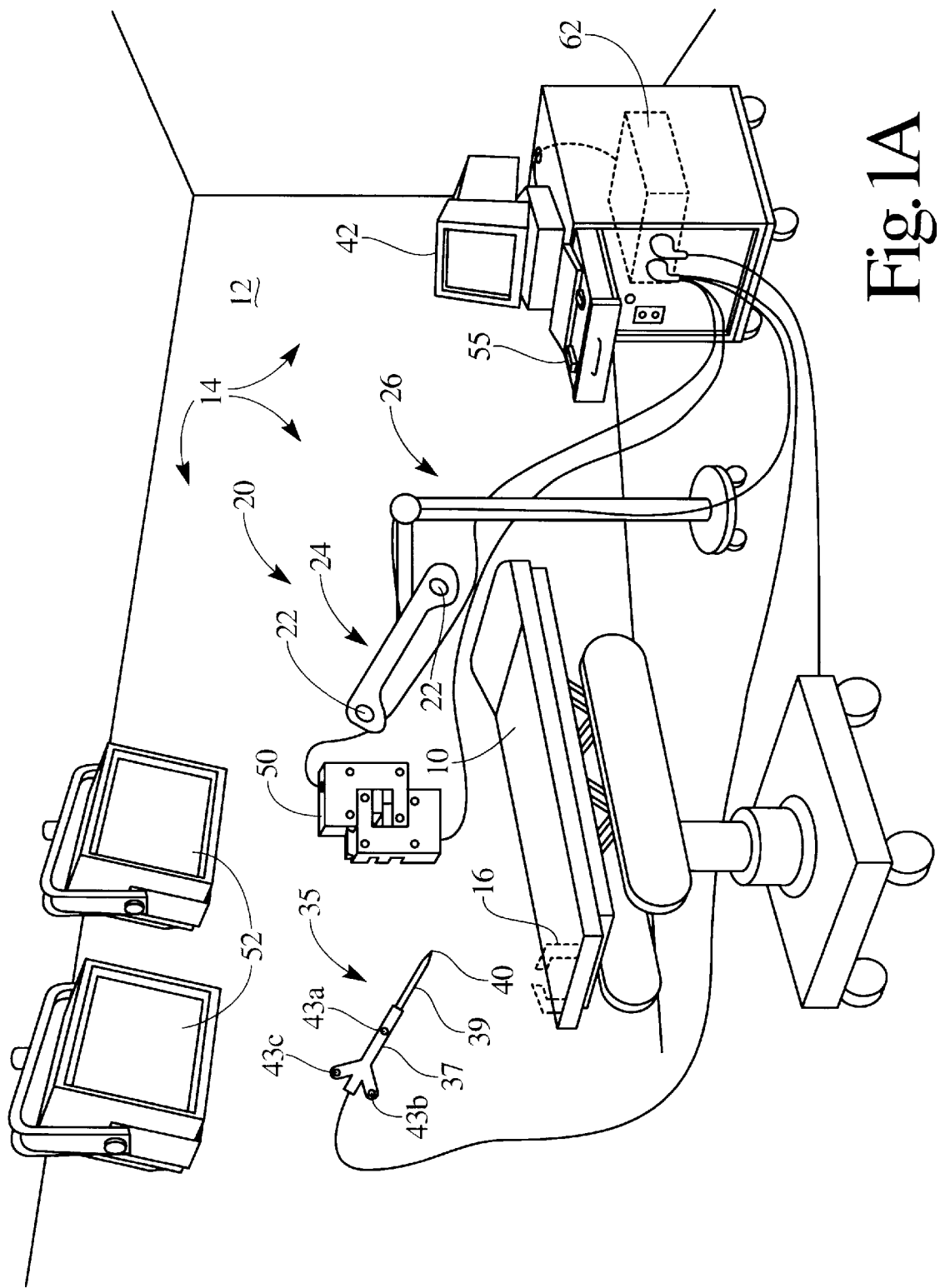

TOOL CALIBRATOR

TECHNICAL FIELD

The present invention relates to the medical diagnostic and surgical arts. More particularly the present invention relates to a tool calibrator for calibrating tools used in conjunction with various medical procedures including neurosurgery, neurobiopsy, CT-table needle body biopsy, breast biopsy, endoscopic procedures, orthopedic surgery, and the like.

BACKGROUND OF THE INVENTION

Three-dimensional diagnostic images of the brain, spinal cord, and other body portions are produced by diagnostic imaging equipment such as CT scanners, magnetic resonance imagers, and the like. These imaging modalities often provide structural detail with a resolution of a millimeter or better.

Image guided surgery systems have been developed to utilize this data to assist the surgeon in presurgical planning and in accurately locating a region of interest within the body of a patient. In the operating arena, the image guided surgery systems are used to display position and orientation of a surgical tool in its correct location with respect to the images of the patient. Surgical tools typically include a trackable handle portion and a tool head which may be inserted into the patient's body. One example of an image guided surgery system is U.S. Pat. No. 5,517,990, Stereotaxy Wand and Tool Guide, to Kalfas et al. issued May 21, 1996, incorporated by reference herein.

Three and sometimes four views of image data are displayed on a monitor visible to the surgeon. These views typically include axial, sagittal, and coronal views of the patient. A fourth oblique view is sometimes displayed, presenting image data in a plane orthogonal to a tip of the tool. The location of the tip of the tool, the tool's trajectory, and diameter of the tool head are displayed on one or more of these images. The algebraic distance between the tip of the tool and a desired position may also be displayed numerically on the monitor.

Given the nature of image guided surgery procedures, it is necessary to be able to track the location of the tip of the tool, the tool's trajectory, and diameter of the tool head with a high degree of precision, often requiring calibration to less than a millimeter in accuracy. The tools are tracked in an operating room or other area by use of a tracking system or localizer. The tracking system tracks the tools by virtue of three or more spaced apart position signaling devices, such as infrared emitters or reflectors, connected to the tool in a fixed relation thereto. The position signaling devices are positioned in a unique pattern for each tool in order to allow the tracking system to be able to distinguish one tool from another. In other words, the unique pattern can be said to characterize the tool.

A central computer coupled to the tracking system is preprogrammed with information related to where the tip and trajectory of each tool is with respect to the tool's position signaling devices and with information related to the diameter of the tool head. For instance, with respect to a tracked probe having three infrared emitters, the central computer maintains information related to where the tip of the probe is with relationship to a selected point on a plane defined by the three infrared emitters. Based on this information, a precise location of the tip can be calculated by the central computer and displayed on one of the monitors.

In a variety of surgical tools such as drills, probes, endoscopes, etc. it is often beneficial to a surgeon or other individual to make changes to the tool which may affect the positioning of the tip as well as the diameter of the tool head. For instance, on a surgical drill it is often helpful for the surgeon to be able to change the size and length of a drill bit situated in the tool to accommodate different surgical procedures. Further, with respect to the probes, it is often desirous to replace different length and diameter shafts on the probe handle in order to reach different regions in the patient.

Unfortunately, because the position of the tip of each tool with respect to the tool's position signaling devices are preprogrammed into a memory associated with each tool and passed along the central computer along with information on the diameter of the tool head, changes to the tool which affect the location of the tip and diameter of the tool head cannot easily be made. If changes are made, an operator needs to determine the new relationship between the tip of the tool and the tool's position signaling devices and enter this information into the central computer. Further, information related to a new diameter of the tool head may also need to be entered. This process is time consuming and cumbersome. If the new information is not entered into the central computer, the tip of the tool will not be properly tracked and displayed on the monitor.

The present invention provides a new and improved method and apparatus for calibrating a surgical tool which addresses the above-referenced matters, and others.

SUMMARY OF THE INVENTION

A tool calibrator includes two movable blocks shaped to slidably engage and secure a tool in a desired position. The tool is secured by a series of staggered V shaped grooves on each of the two movable blocks having a known geometrical relationship with a diameter of a tool head of the tool. The tool calibrator further includes at least one position signaling device for communicating a location of the tool calibrator in an operating room or other area. A position and direction of a tip of the tool is determined by comparing a location of the tool secured within the tool calibrator to the location of each of the two movably blocks. Further, based on the location of each of the two movable blocks, the diameter of the tool head is calculated.

In a preferred embodiment, the tool calibrator is able to calibrate a location of a tip of a tool, a direction in which the tip is pointing, and a diameter of a tool head all at once. The direction in which the tip of the tool is pointing is determined by comparing a relationship between position signaling devices connected to each of the two movable blocks securing the tool with position signaling devices connected to the tool. The location of the tip of the tool is determined by comparing the location of the position signaling devices connected to the tool calibrator to the location of position signaling devices connected to the tool. The diameter of the tool is determined by virtue of a known geometrical relationship between the V shaped grooves of two movable blocks and the diameter of the tool head.

In accordance with the present invention, a tool for determining an attribute of a surgical tool is provided. The tool including a means for positioning a tip of the surgical tool to a desired location of the tool and a position signaling device fixed in relation to the desired location.

In accordance with another aspect of the present invention, a system for determining an attribute of a surgical tool is provided. The system including a tool, a means for tracking the signaling device; and a means for processing information tracked by the means for tracking. The tool includes a means for securing a tip of the surgical tool to a desired location, and a signaling device fixed in relation to the desired location.

In accordance with still another aspect of the present invention, a tool for determining an attribute of a surgical tool is provided. The tool including a first portion, a second portion movable in relation to the first portion, at least one position signaling device fixed in relation to the first portion, and at least one position signaling device fixed in relation to the second portion.

In accordance with yet another aspect of the present invention, a method of determining an attribute of a surgical tool for use in an image guided surgery system is provided. The method includes the steps of positioning a tip of the surgical tool to a desired location which is fixed in relation to a position signaling device, securing the surgical tool in place in relationship to the desired location, and sensing by a component of the image guided surgery system a location of the position signaling device.

In accordance with another still another aspect of the present invention, a method of determining an attribute of a surgical tool for use in an image guided surgery system is provided. The method includes the steps of, positioning a tool head of the surgical tool with respect to a first portion, securing the tool head into a desired position with respect to the first portion using a second portion, the first portion and the second portion slidably engaging with one another, sensing a position of the first portion, and sensing a position of the second portion.

To the accomplishment of the foregoing and related ends, the invention then, comprises the features hereinafter fully described and particularly pointed out in the claims. The following description and the annexed drawings set forth in detail certain illustrative embodiment of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 1a is a perspective view of an operating room in which the present invention is deployed;

DETAILED DESCRIPTION OF THE PREFERRED EMBODIMENTS

Figure 1B:
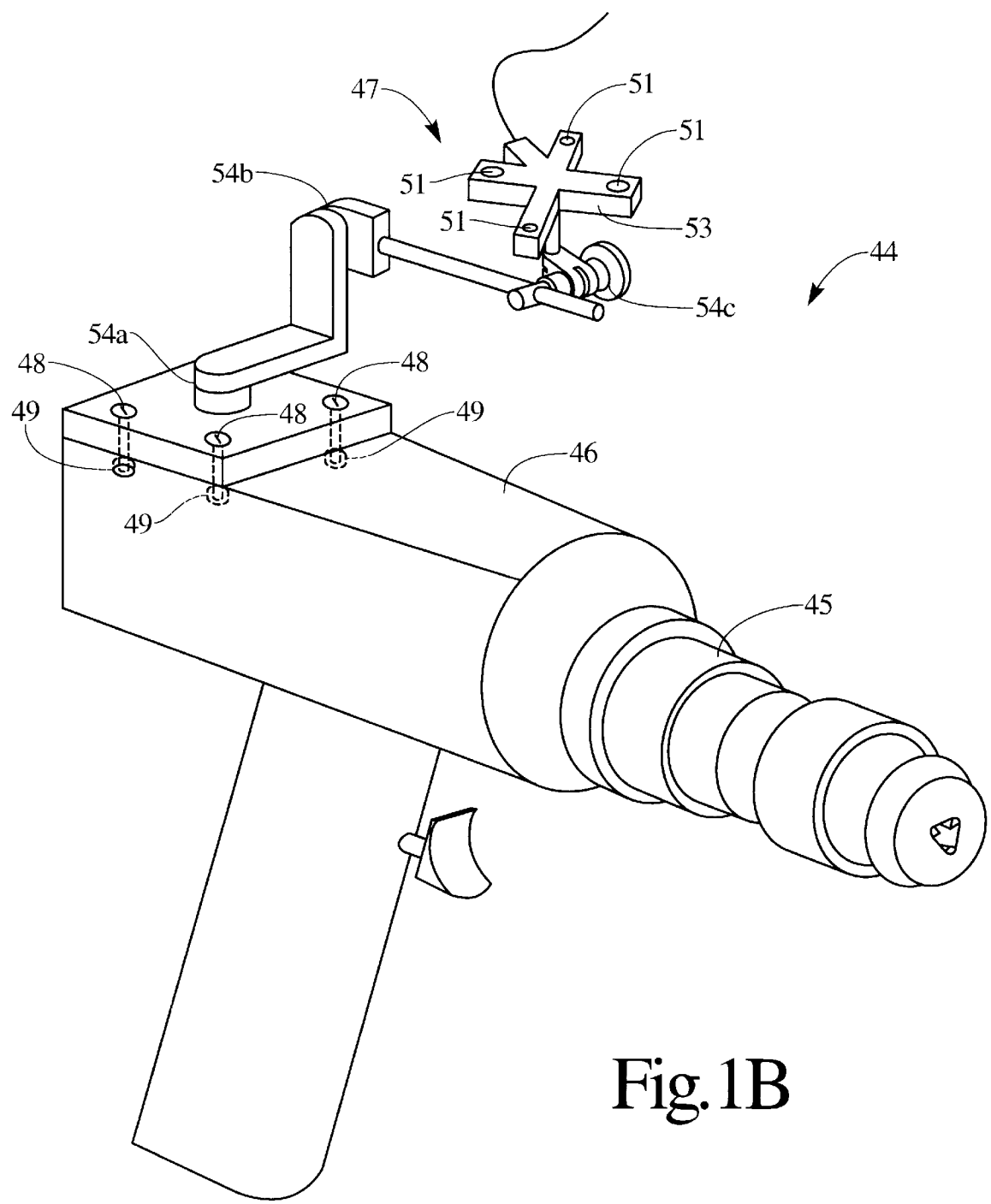
FIG. 1b is a perspective view of a drill with a removable reference frame target for use in the operating room of FIG. 1.

The present invention will now be described with reference to the drawings in which like reference numerals are used to refer to like elements throughout.

With reference to FIG. 1a, a patient (not shown) is received on an operating table or other subject support 10 and appropriately positioned within an operating or surgical room 12 having an image guided surgery system shown generally at 14. A securing means such as a head clamp 16 securely positions a portion of the patient or subject under consideration. A locating device 20 such as an infrared localizer determines the location and orientation of at least one surgical tool. Tools refers to any instrument or apparatus in the surgical room which is tracked by the locating device 20.

In the preferred embodiment, the locating device 20 is an infrared localizer such as the Polaris™ localizer system supplied by Northern Digital, Inc. of Waterloo, Ontario, Canada. The localizer system includes two spaced apart infrared cameras 22 mounted on a sensor head 24. The sensor head 24 is in turn mounted in a fixed position within the operating room 12, for example on a stand 26 resting on the floor. The cameras 22 may be mounted in another known position in the operating room 12, such as to the ceiling or wall or to the subject support 10. Of course, other locating devices, such as ultrasonic, optical, RF, or electromagnetic localizers, may be used. The surgical tool may also be mounted to an articulated arm, the arm functioning as the locating device.

A surgical tool 35 such as a surgical probe, drill or endoscope, is shown to have a handle portion 37 and an interchangeable tool head 39. Locations on the tool 35 are defined with respect to a local tool reference frame. For example, the tool reference frame may be defined such that an origin is at a point on the handle of the tool 35 and having an axis substantially collinear with a pointing axis of the tool 35. The tool 35 includes at least three position signaling devices 43a, 43b, 43c, collectively referred to as position signaling devices 43, such as infrared or sonic emitters or reflectors, having a known relationship to the tool reference frame. Additional position signaling devices 43 may be used to provide a redundant indication in case the line of sight between one of the position signaling devices 43 and the cameras 22 is blocked or to permit more accurate determination of the position of the tool 35. Based on the signals detected by the camera 22, the location and orientation of the tool 35 and hence the tool reference frame with respect to the cameras 14 and hence the operating room reference frame are determined.

In the event a tool does not come pre-equipped with position signaling devices 43 or existing position signaling devices 43 are not adequately located with respect to the tool 35 for communicating with the locating device 20, a removable reference frame target may be affixed to the tool 35. For instance, as shown in FIG. 1b, a drill 44 includes an interchangeable drill head 45 and handle portion 46 securing the drill head 45. The drill 44 does not include position signaling devices 43 directly attached to the handle portion 46. As such, a removable reference frame target 47 is shown attached to the handle portion 46 of the drill 44. More specifically, the reference frame target 47 is rigidly attached to the handle portion 46 of the drill 44 by securing flat head screws 48 into corresponding threaded apertures 49 on the handle portion 46 of the drill 44. The reference frame target 47 may also be attached by way of a clamp or in other ways. Four position signaling devices 51 are located on a cross shaped target 53 to provide the drill 44 with a reference frame capable of being sensed by locating device 20. Although four position signaling devices 51 are shown, three or more position signaling devices could be used. Depending on the type of locating device 20 in the operating room 12, the position signaling devices may be infrared emitters, sonic emitters, RF emitters, or reflectors, for example. The target 53 may be rotated and fixed in a desirable location with respect to the tool 44 by virtue of lockable joints 54a, 54b, 54c. It will be appreciated that the removable reference frame target 47 allows any device to be tracked in the image guided surgery system by the locating device 20. For instance, the reference frame target 47 may be attached to common household tools, surgical instruments, or any other object. Further, if the object upon which the reference frame target 47 is attached includes a tool head and/or a tip of which it would be desirous to track with respect to images shown on a monitor in an operating room, the present invention allows a way of accurately and rapidly determining such attributes and storing them in the central computer 42 as described in detail below.

In order to properly track a location of the a tip 40 of the tool 35 with respect to the tool reference frame, information related to an offset between a selected point on the tool reference frame and the tip 40 of the tool 35 may be preprogrammed into a computer system 42 or calibrated via a surgical tool calibrator 50. Details related to the structure and operation of the tool calibrator 50 is discussed in more detail below. Tracking a precise location of the tip 40 of the tool 35 is necessary to ensure proper relationships between the tip 40 of the tool 35 and a patient's anatomy are correlated. More specifically, in image guided surgery procedures it is often the case that a tracked position and trajectory of the tip 40 of the tool 35 is superimposed on images of the patient and displayed to the surgeon and other individuals via monitors 52 or in some other fashion. The surgeon typically relies on the displayed results to help complete a procedure at hand.

Figure 2:
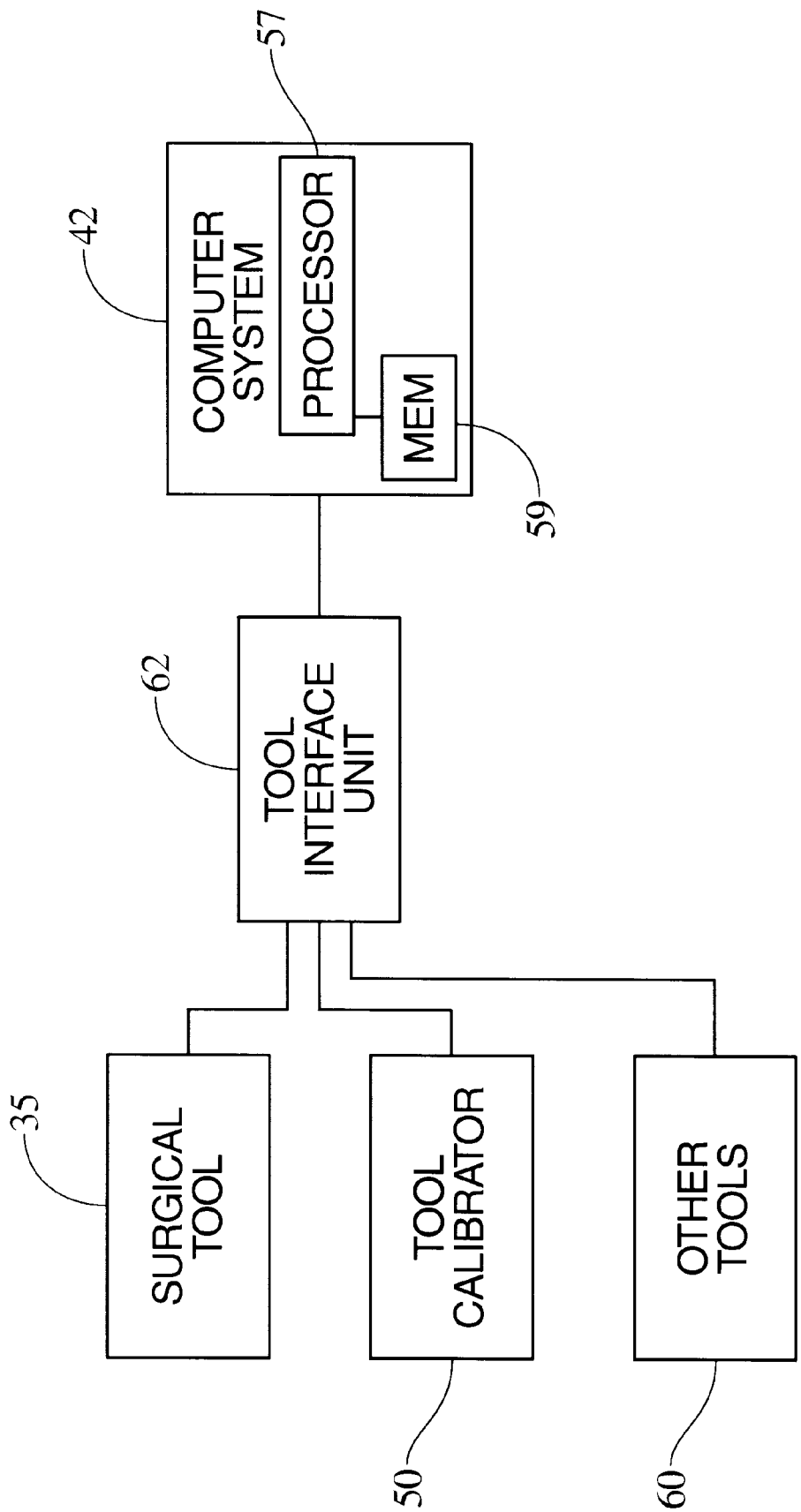
FIG. 2 is a block diagram of a system according to the present invention.

With continued reference to FIG. 1a and further reference to FIG. 2, an operator console 55 supports the computer system 42. Alternately, the computer system 42 can be remotely located and connected with the operator console 55 by cabling. The computer system 42 includes a processor 57 and a data memory 59 coupled to the processor 57. The data memory 59 contains data indicative of a three-dimensional image of the patient or subject. Because the data can be visualized as a three-dimensional rectangular grid, selectable orthogonal and other oblique planes of the data can be readily withdrawn from the data memory 59 using conventional technology. Such data may, for example, be displayed on the overhead monitors 52 in the operating room 12 for convenient viewing by the surgeon.

The surgical tool 35, tool calibrator 50 and other tools 60 are coupled to the computer system 42 through a tool interface unit 62. The tool interface unit 62 serves to perform coordinate transformation between these devices prior to passing along information to the computer system 42 for further processing. Similar to the discussion above with respect to the surgical tool 35, each of the tools in the operating room 12 including the tool calibrator 50 may be defined by a local reference frame which is oriented in respect to the operating room reference frame by the tool interface unit 62.

Based on information sensed by the cameras 22 and passed along to the tool interface unit β, the transforms between the patient, tools and operating room reference frames can readily be calculated. As is well known in the art, a transform is accomplished by determining an offset $X_{offset}$, $Y_{offset}$, $Z_{offset}$ between the reference frames to be transformed. These values of $X_{offset}$, $Y_{offset}$, $Z_{offset}$ are added to or subtracted from the coordinates of one of the reference frames as required to translate between the two. The coordinate systems are then rotated relative to each other about their origins by angles α, β, γ so that their respective x, y and z axes coincide.

Referring now to FIGS. 3–7, the tool calibrator 50 of the preferred embodiment is shown in more detail. The tool calibrator 50 includes two slidably interfacing blocks 70a and 70b. In the preferred embodiment, the blocks 70a, 70b are each made of aluminum, although any other durable material including other metals, plastic, or wood could alternatively be used. Block 70a includes a front face 72a, a top surface 74a, and a bottom surface 76a. Similarly, block 70b includes a front face 72b, a top surface 74b, and a bottom surface 76b.

Figure 3:
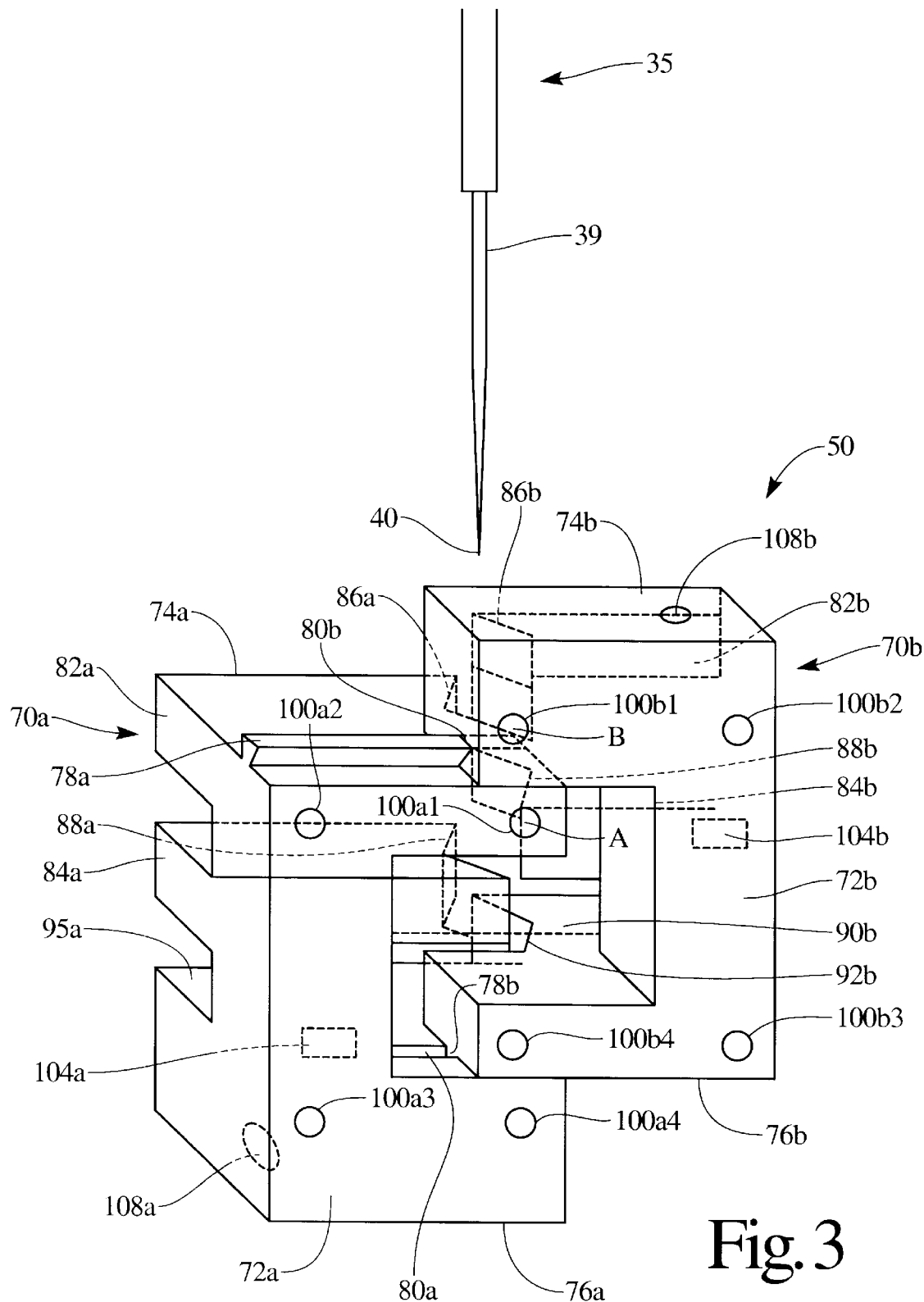
FIG. 3 is an isometric view of the tool calibrator of the preferred embodiment of the present invention.
Figure 4:
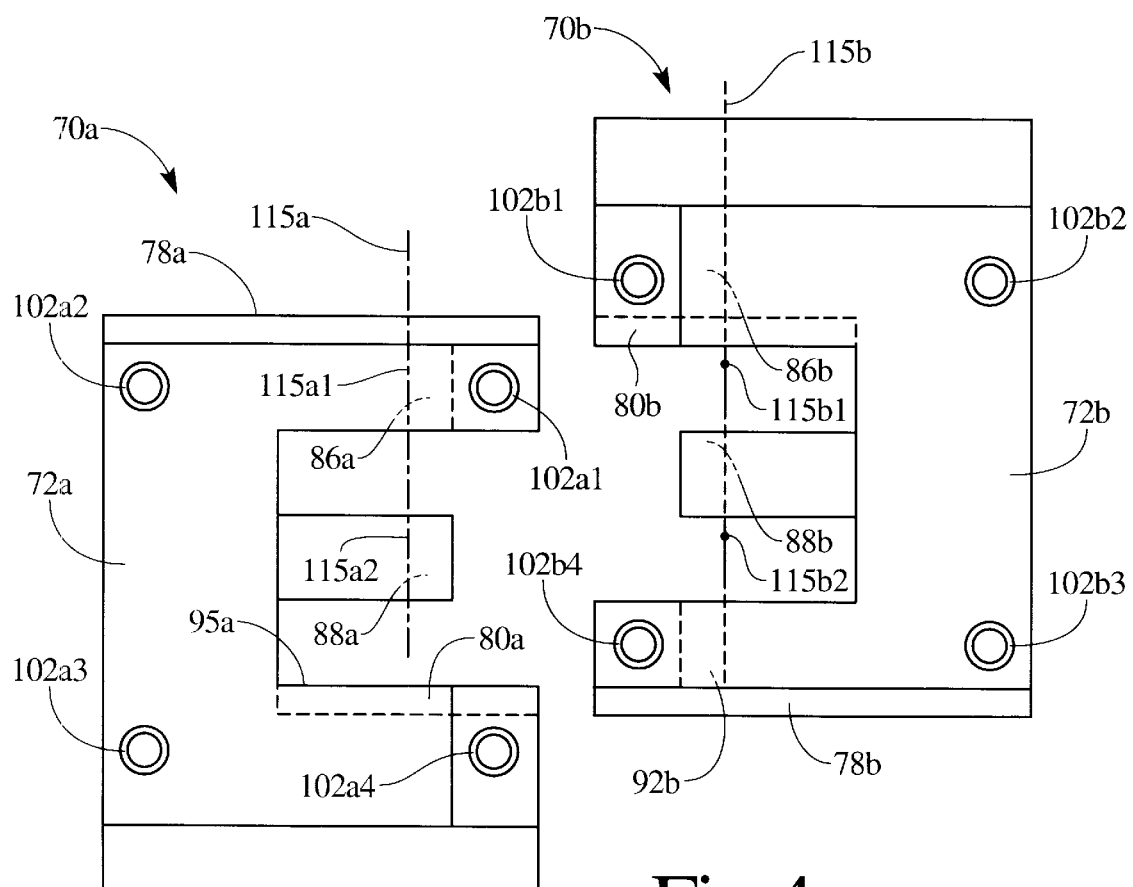
FIG. 4 is front view of each block of the tool calibrator of FIG. 3.

As best seen in FIGS. 3 and 4, blocks 70a and 70b are shaped to slidably engage by way of a pair of mating V shaped tongue and grooves. More specifically, the top surface 74a of block 70a and the bottom surface 76b of block 70b each include a V shaped tongue 78a, 78b, respectively. The tongues 78a, 78b are shown to each extend across a full distance of their respective surfaces 74a, 76b. A mating groove 80a for tongue 78b is located on a side of the block 70a closer to the bottom surface 76a. A mating groove 80b for tongue 78a is located on a side of the block 70b closer to the top surface 74b. Each mating groove 80a, 80b is sized to receive its mating tongue 78b, 78a, respectively, such that a substantially no movement is allowed in any direction except for the direction of slide.

Figure 5:
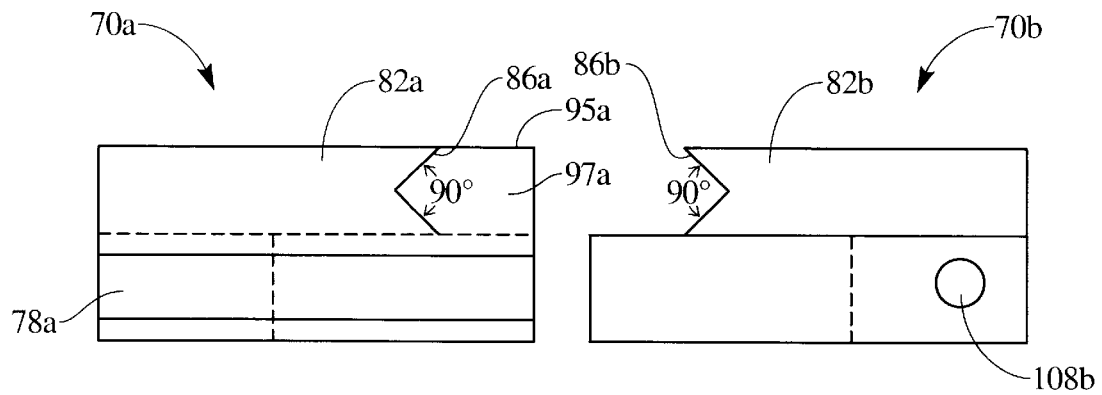
FIG. 5 is a top view of each block of the tool calibrator of FIG. 3.

In order to position, secure and determine a size of a tool head introduced to the tool calibrator 50, block 70a includes staggered finger portions 82a and 84a, and block 70b includes staggered finger portions 82b and 84b. Each of the finger portions 82a, 82b, 84a, 84b, is positioned such that it partially interlocks one on top of the other when the blocks 70a, 70b are positioned in a closed position such as that shown in FIG. 1a. As best seen in FIGS. 3, and 5, an end of each finger portion 82a, 82b, 84a, 84b includes a V shaped groove portion 86a, 86b, 88a, 88b, respectively. Further a bottom portion 90b of block 70b also includes a V shaped groove 92b. The V shaped groove portions 86a, 86b, 88a, 88b, 92b of the present embodiment are each at 90 degree angles, although any suitable angle could be selected. Further, although the groove portions 86a, 86b, 88a, 88b, 92b of the present embodiment are described with respect to having a V shape, other shapes or combination of shapes including, circular, octagonal and the like may also be used. It will be also be appreciated that the term V shaped is not exclusive of shapes which have a precise corner, but rather includes substantially V shaped grooves having corners which are curved or otherwise shaped.

As best seen in FIG. 4. the V shaped groove portions 86a, 88a, on block 70a and the V shaped groove portions 86b, 88b, 92b, on block 70b each define a respective axis 115a, 115b. As shown in FIG. 4, the axis 115a associated with block 70a is substantially orthogonal to the surface 97a and coincides with corners of the 90 degree angle formed by V shaped grooves 86a, and 88a. The axis 115b associated with block 70b is also substantially orthogonal to the surface 97a when block 70b is coupled to block 70a, and the axis 115b coincides with corners of the 90 degree angle formed by the V shaped grooves 86b, 88b, 92b.

As best seen in FIGS. 3 and 5, block 70a includes surface 95a upon which tool tips 40 to be calibrated are positioned. More specifically, tool tips to be calibrated are positioned in a region 97a on surface 95a shown in hashed lines in FIG. 5. The precise location of the tip 40 of the tool 35 in the region 97a prior to calibration is based on a diameter D (see FIG. 8) of the tool head 39 and the angle of the V shaped grooves 86a, 86b, 88a, 88b, 92b.

In order to accommodate tracking of each block 70a, 70b of the tool calibrator 50 by the camera 22, each block 70a, 70b includes four position signaling devices $100_{a1}$, $100_{a2}$, $100_{a3}$, $100_{a4}$, and $100_{b1}$, $100_{b2}$, $100_{b3}$, $100_{b4}$, collectively referred to as position signaling devices 100, situated on the front face 72a, 72b of the blocks 70a, 70b, respectively. The position signaling devices 100 of the preferred embodiment are infrared emitters for use with an infrared locating device, although reflectors, sonic emitters, RF emitters, or other devices could be used depending on the characteristics of the locating device 20 being used. The position signaling devices are affixed or mounted to stepped aperatures $102_{a1}$, $102_{a2}$, $102_{a3}$, $102_{a4}$, and $102_{b1}$, $102_{b2}$, $102_{a3}$, $102_{a4}$, on the front face 70a, 70b, of each block (see FIG. 4). Although the present embodiment shows four position signaling devices 100 disposed on each block 70a, 70b, it will be appreciated that only three such position signaling devices are needed on each block 70a, 70b, for complete tracking of the tool calibrator 50 in the preferred embodiment.

Referring to FIG. 3, disposed within each block 70a, 70b, is a memory chip 104a, 104b, respectively. The memory chip 104a contains information related to the positioning of the position signaling devices 100a disposed on block 70a with respect to a selected point associated with the local reference frame of block 70a. In the preferred embodiment, the point from which the position signaling devices 100a is calculated is point A located at a center of the position signaling device $100_{a1}$. Similarly, memory chip 104b contains information related to the positioning of the position signaling devices $100_b$ disposed on block 70b with respect to a selected point associated with the local reference frame of the block 70b. In the preferred embodiment, the point from which the position signaling devices 100b is calculated is point B located at a center of the position signaling device 100b1.

Figure 6:
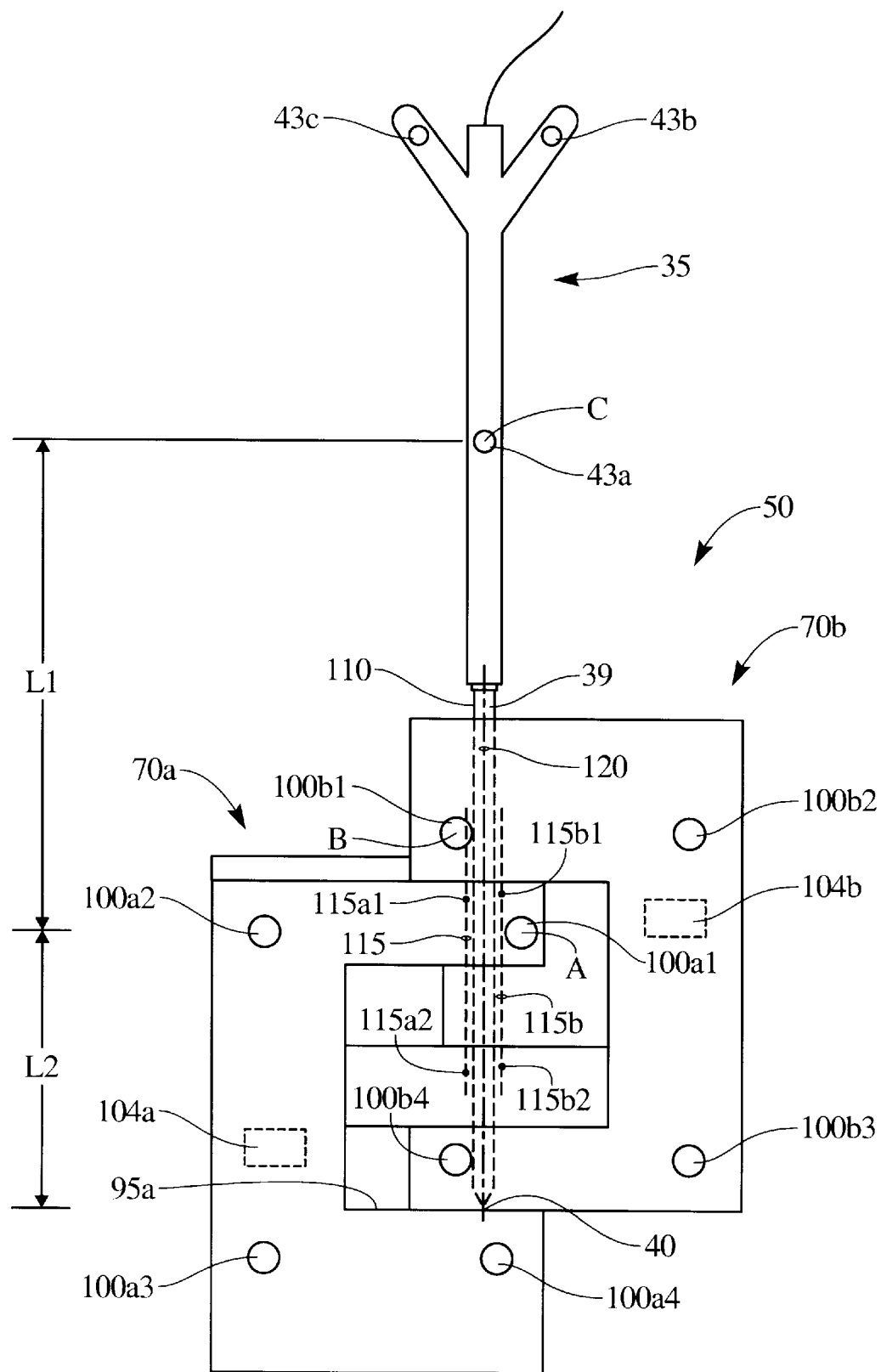
FIG. 6 is a front view of tool calibrator of FIG. 3 receiving a tool for calibration.

Referring now to FIG. 6, the position of the axis 115a with respect to the selected point A associated with block 70a is also stored in the memory 104a and passed along to the tool interface unit 62. The position of the axis 115a is stored by determining two offset values between point A and two points $115_{a1}$, and $115_{a2}$ on the on the axis 115a. The offset values are each stored as three dimensional offset values in the x, y and z directions as defined with respect to the three dimensional local reference frame of block 70a. A location of the surface 95a with respect to the point A is also similarly stored in the memory 104a and passed along to the tool interface unit 62.

The position of the axis 115b is defined with respect to the selected point B on block 70b. As with block 70a, two offset values between point B and two points $115_{b1}$, and $115_{b2}$ on the axis 115b are stored in the memory 104b and passed along to the tool interface unit 62. The offset values include three dimensional offset values in the x, y, and z directions and are stored with respect to the local reference frame of block 70b.

The information from the memory chips 104a, 104b, along with power and control signals are provided between the blocks 70a, 70b to the tool interface box 62 via a seven pin female connector 108a, 108b connected to each block 104a, 104b, respectively. It will be appreciated that although points A and B are selected in the preferred embodiment to be located at the center of the position signaling devices $100_{a1}$, $100_{b1}$, respectively, any location for points A and B could be selected with respect to the local reference frame of each block 70a, 70b.

Figure 7:
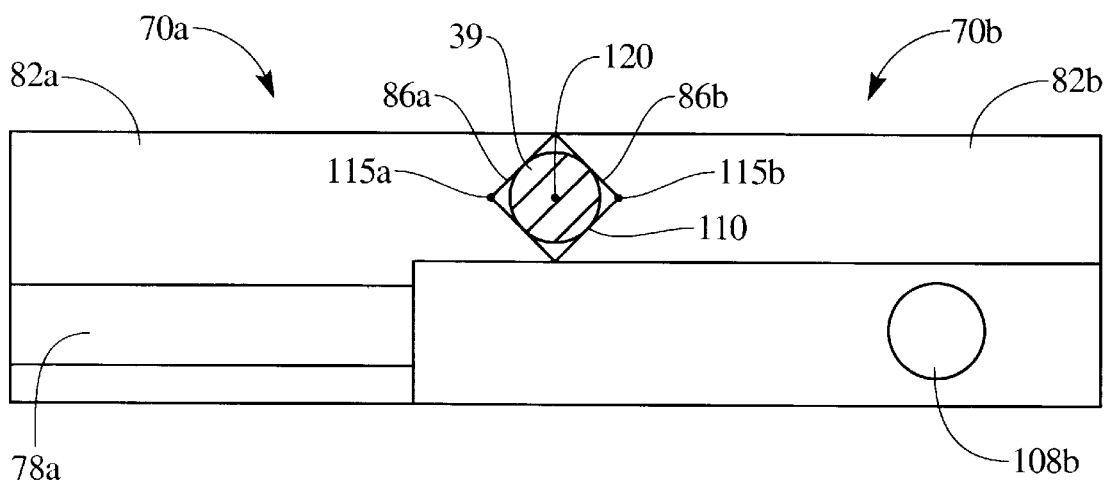
FIG. 7 is a top view of the tool calibrator of FIG. 6 with a partially sectioned view of the tool.

Referring now to FIGS. 6 and 7, the operations of the preferred embodiment will be discussed. The tool calibrator 50 of the present invention can be used to determine several attributes of a surgical tool in a one step process. The attributes include determining a location of a tip of a tool with respect to the tool's local reference frame, a direction or trajectory in which a tool head is pointing with respect to the tool's local reference frame, and a diameter of a tool head. A surgeon may for instance desire to determine attributes of a tool or a number of tools prior to beginning a procedure so that an image of the tool(s) shown on the monitor 52 shows the correct position and orientation of the tool. Additionally, the surgeon may use the tool calibrator 50 of the present invention to re-calibrate a tool during surgery in the event an existing tool head on the tool is exchanged for a tool head having different dimensions. Thus, for example, if a different size drill bit for a drill is needed during a surgery, the surgeon could quickly and efficiently re-calibrate the drill so images of the drill with the new drill bit is correctly represented on the monitors 52.

In order to calibrate a tool such as the tool 35, an individual initially slides block 70b into a position with respect to block 70a such that an opening defined by the staggered V shaped groove portions 86a, 86b, 88a, 88b, 92b is large enough to readily accept the tool head 39. The tip 40 of the tool head 39 is then positioned onto the region 97a of the surface 95a of block 70a. Next, the user secures the tool head 39 in place by sliding block 70b into a relationship with block 70a such that an outer diameter 110 of the tool head 39 is fixed in place by the V shaped groove portions 86a, 86b, 88a, 88b, 92b, as best shown in FIG. 7. Once completed, the user situates the tool calibrator 50 such that the position signaling devices 100 of the tool calibrator 50 and the position signaling devices 43 of the tool 35 are all detectable by the cameras 22. Finally, the user inputs a command to the computer system 42 indicating that a new tool calibration is taking place such that the computer system 42 records the information detected.

The location of the tip 40 of the tool 35 along with the direction in which the tip 40 is pointing is determined in the preferred embodiment by comparing the two axes 115a, 115b as best seen in FIGS. 4 and 6. Once the position of axis 115a and 115b and surface 95a with respect to the operation room are known by the tool interface unit 62 and computer system 42, the computer system 42 determines the direction of the tool head 39 and the location of the tip 40 with respect to the local reference frame of the tool 35. The direction of the tool head 39 with respect to the local reference frame of the tool 35 is determined by the computer system 42 by calculating a location of a longitudinal axis 120 of the tool head 39. More specifically, once the tool head 39 is secured into position by the V shaped grooves 86a, 86b, 88a, 88b, 92b, the axis 120 of the tool head 39 is located half way between axis 115a and 115b. Thus, by calculating a half way point between the two axes 115a and 115b, the axis 120, and therefore, the direction in which tip 40 is pointing is readily determined.

Referring now to FIG. 6, a location of the tip 40 is calculated by calculating offset values between a selected point associated with the tool 35 and a selected point associated with the tool calibrator 50. In the preferred embodiment, the selected point with respect to the tool 35 is point C located at the center of the position signaling device 43a. Further the selected point for the tool calibrator 50 is the point A. As both point C and point A are tracked by cameras 22, a precise offset between these points is readily determinable. In the present example, an offset between point C and point A is shown to be some value L1. Further, an known offset L2 between the point A and the surface 95a is known and stored in the memory 104a. Thus, by knowing the full offset value (equal to L1+L2) the tip 40 is located from point C, and that the tip 40 is located along the axis 120 of the tool 35, the precise location of the tip 40 with respect to the local reference frame of the tool 35 can be calculated as is well known in the art. It will be appreciated that although the offset from the location of the tip 40 in the present example is calculated with respect to points A and C, any two points with respect to the local reference frame of the tool calibrator 50 and tool 35, respectively, could have been used.

Figure 8:
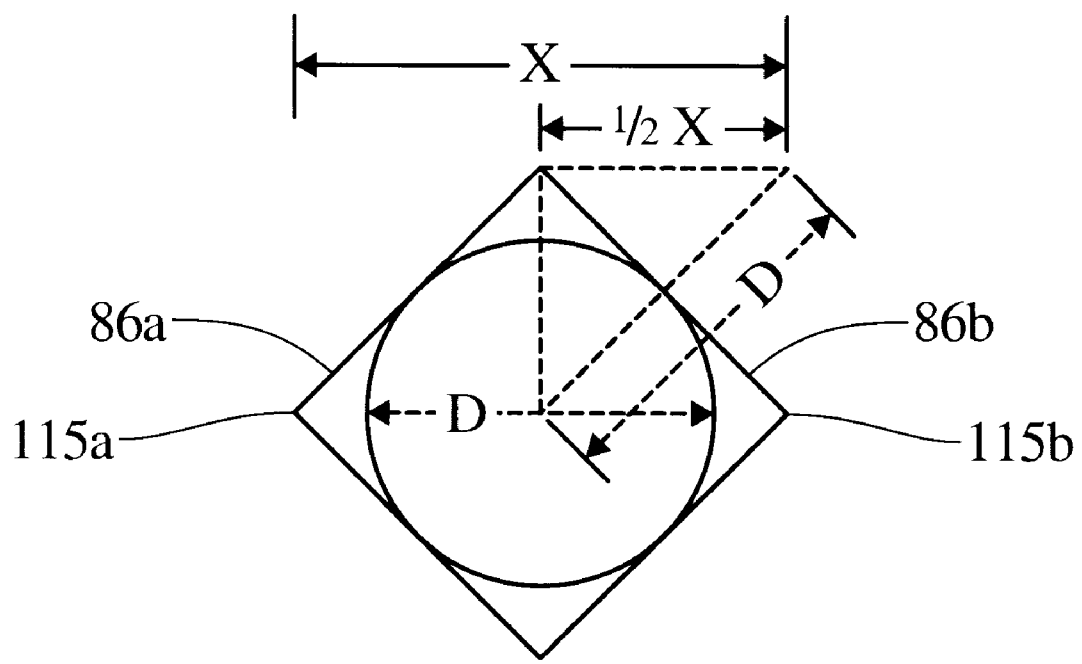
FIG. 8 shows a geometrical relationship between the tool calibrator of FIG. 3 and a diameter of a tool head of the tool.

Referring now to FIG. 8, calculations related to determining tie diameter D of the tool head 39 is discussed in more detail. As discussed above, the corner of each V shaped groove 86a, 86b, 88a, 88b, 92b is angled at 90 degrees. Therefore, regardless of the diameter of the tool head 39, a top view of the staggered V shaped grooves 86a, 86b, 88a, 88b, 92b supporting the tool head 39 as shown in FIGS. 7 and 8 is always in the shape of a square. By use of geometry, the diameter D of the tool head may be readily calculated. More specifically, by knowing the location of axis 115a and 115b, as discussed above, the computer system is able to determine a distance X between the two axis. Next, by visualizing an equilateral triangle in which the hypotenuse is equal to the diameter D of the tool head, the diameter is readily calculatably using known geometrical relationships. In the present invention the relationship between the diameter D and distance X is thus represented by the equation:

$$\left(\frac{1}{2}*X\right)^2 + \left(\frac{1}{2}*X\right)^2 = D^2$$

Upon solving for the diameter D, it is found that the diameter D is equal to approximately 0.7071 *X. Of course, in the event the V shaped grooves 86a, 86b, 88a, 88b, 92b are angled at an angle other than at 90 degrees, other known geometrical relationships could readily be used to calculate the diameter D of the tool head 39. Thus using the tool calibrator 50 of the present invention, the location of the tip 40, direction in which the tip 40 is pointing, and diameter D of the tool head 39 is able to be calibrated all at once.

In an alternative embodiment of the present invention, the tool calibrator 50 does not include any position signaling devices 100. Rather, at a location of which a center point of each of the position signaling devices 100 (see FIG. 3) in the embodiment discussed above would be, a divot is placed on the front surface 72a, 72b of the blocks 70a, 70b. Alternatively, a dot, cross, or other marking could be drawn or etched on the surface to indicate a positioning of the center points.

In order to calibrate a tool introduced to the tool calibrator 50 of the alternative embodiment, a user would position the tool into the tool calibrator 50 in a similar fashion as described above. Once the tool is positioned and secured in the tool calibrator 50 the user would then place the tool calibrator on a surface or otherwise ensure that the tool calibrator is fixed in location with respect to the operating room reference frame. Next, the user would take a properly tracked probe, such as probe 35 (see FIG. 1a) and touch the tip 40 of the probe on each of the divots or markings and register their locations in the computer system. Once such information is recorded in the computer system, the location of the tip of the tool being calibrated, the direction of the tool head of the tool and the diameter of the tool head could all be determined in the same fashion as described above with reference to the preferred embodiment.

The invention has been described with reference to the preferred embodiments. Obviously, modifications and alterations will occur to others upon reading and understanding the preceding detailed description. For instance, in the preferred embodiment discussed above, each block 70a and 70b is shown to have a sufficient number of position signaling devices 100 to define a plane in which each to the blocks 70a, and 70b are located. However, since the front faces 72a, 72b of each block 70a and 70b remain in the same plane when connected together, it is possible to place two position signaling devices on one of the blocks 70a, 70b and only one position signaling device on the other of the blocks 70a and 70b, and used the combined information from both blocks 70a and 70b to determine the plane in which the combination resides. Further, if information related to the position of the axis 120 of the tool 35 is already known by the computer system 42, and only a length of the tool head 39 is changed, it is possible that only one position signaling device 100 needs to be associated with the entire tool calibrator 50 to calculate a positioning of the new tip 40. For instance, a single position signaling device could be placed on or adjacent the surface 95a upon which the tip 40 of the tool 35 comes into contact during calibration, and a single offset value between point C on the tool 35 and the one position signaling device on the tool calibrator 50 could be measured. It is intended that the invention be construed as including all such modifications and alterations insofar as they come within the scope of the appended claims or their equivalence thereof.

What is claimed is:

1. A tool for determining an attribute of a surgical tool, the tool comprising:
   means for positioning a tip of the surgical tool to a desired location of the tool; and
   a position signaling device fixed in relation to the desired location, wherein the position signaling device is adapted for operative communication with an image guided surgery system.

2. The tool according to claim 1, wherein the means for positioning comprises means for determining a trajectory of a tool head of the surgical tool.

3. The tool according to claim 1, wherein the means for positioning the tip of the surgical tool includes a first portion and a second portion.

4. The tool according to claim 3, wherein each of the first portion and the second portion includes at least one V shaped groove.

5. The tool according to claim 4, wherein an angle of each of the at least one V shaped groove is substantially 90 degrees.

6. The tool according to claim 5, wherein the first portion and the second portion include a slidable interface.

7. The tool according to claim 3, comprising at least three position signaling devices disposed on the first portion and at least three position signaling devices disposed on the second portion.

8. The tool according to claim 7, wherein each of the position signaling device comprises one of a reflective element and an infrared emitter.

9. The tool according to claim 1 wherein the means for positioning comprises means for determining a diameter of the surgical tool.

10. The tool according to claim 9, wherein the desired location is on a surface of the tool having a plane substantially orthogonal to a longitudinal axis of the surgical tool.

11. A system for determining an attribute of a surgical tool, the system comprising:

a tool including:
- means for securing a tip of the surgical tool to a desired location; and
- a signaling device fixed in relation to the desired location;

means for tracking the signaling device; and means for processing information tracked by the means for tracking.

12. The system according to claim 11, wherein the means for securing the tip of the surgical tool comprises means for determining a diameter of a tool head of the surgical tool.

13. The system according to claim 12, wherein the means for securing the tip of the surgical tool includes a first portion and a second portion.

14. The system according to claim 13, wherein the first portion and the second portion include a slidable interface.

15. The system according to claim 14, comprising at least three position signaling devices disposed on the first portion and at least three position signaling devices disposed on the second portion.

16. The system according to claim 15, wherein each of the position signaling device comprises one of a reflective element and an infrared emitter.

17. The system of claim 11, wherein the means for processing information tracked by the means for tracking is a computer system.

18. The system of claim 17, wherein the means for tracking is an infrared localizer.

19. The system of claim 18, further comprising:
- a means for displaying the location of the tip of the surgical tool with respect to an object.

20. The system of claim 19, wherein the means for displaying the location of the tip is a monitor.

21. A method of determining an attribute of a surgical tool for use in an image guided surgery system, the method comprising the steps of:
- positioning a tip of the surgical tool to a desired location, the location fixed in relation to a position signaling device;
- securing the surgical tool in place in relationship to the desired location; and
- sensing by a component of the image guided surgery system a location of the position signaling device.

22. The method according to claim 21, further comprising the step of
- sensing by the component of the image guided surgery system a location of the surgical tool.

23. The method according to claim 22, wherein the desired location is on a first portion and the step of securing the surgical tool in place comprises the step of:
- sliding a second portion into position with respect to the first portion such that the surgical tool is secured in place.

24. The method according to claim 23, wherein the first portion and the second portion each include a V shaped groove.

25. The method of according to claim 24, wherein each of the V shaped grooves is at a 90 degree angle.

* * * * *